(12) United States Patent
Domino

(10) Patent No.: US 6,592,621 B1
(45) Date of Patent: Jul. 15, 2003

(54) FLEXIBLE INTRA-OCULAR LENS OF VARIABLE FOCUS

(76) Inventor: Rudolph S. Domino, 310 Bluespring Rd., Princeton, NJ (US) 08540

(*) Notice: Subject to any disclaimer, the term of this patent is extended or adjusted under 35 U.S.C. 154(b) by 0 days.

(21) Appl. No.: 09/710,361

(22) Filed: Nov. 10, 2000

(51) Int. Cl.[7] .................................................. A61F 2/16
(52) U.S. Cl. ...................... 623/6.37; 623/5.13; 623/6.14; 623/6.22
(58) Field of Search ................ 623/5.13, 5.15, 623/6.14, 6.19, 6.22, 6.37, 6.38, 6.39, 6.4, 6.41, 6.42, 6.43, 6.11, 6.44, 6.45, 6.49; 264/156

(56) References Cited

U.S. PATENT DOCUMENTS

| | | | | |
|---|---|---|---|---|
| 3,458,870 A | * | 8/1969 | Stone | 3/13 |
| 4,424,597 A | * | 1/1984 | Schlegel | 3/13 |
| 4,435,050 A | * | 3/1984 | Poler | 351/160 R |
| 4,449,257 A | * | 5/1984 | Koeniger | 3/13 |
| 4,624,669 A | * | 11/1986 | Grendahl | 623/5 |
| 4,693,715 A | * | 9/1987 | Abel, Jr. | 623/5 |
| 4,808,181 A | * | 2/1989 | Kelman | 623/6 |
| 4,810,082 A | * | 3/1989 | Abel, Jr. | 351/160 R |
| 4,842,599 A | * | 6/1989 | Bronstein | 623/5 |
| 4,842,601 A | * | 6/1989 | Smith | 623/6 |
| 4,851,003 A | * | 7/1989 | Lindstrom | 623/5 |
| 4,994,080 A | * | 2/1991 | Shepard | 623/5 |
| 5,019,097 A | * | 5/1991 | Knight et al. | 623/5 |
| 5,133,748 A | * | 7/1992 | Feaster | 623/6 |
| 5,213,721 A | | 5/1993 | Grendahl | |
| 5,282,851 A | * | 2/1994 | Jacob-LaBarre | 623/6 |
| 5,405,385 A | * | 4/1995 | Heimke et al. | 623/6 |
| 5,549,668 A | * | 8/1996 | O'Donnell, Jr. | 623/6 |
| 5,776,191 A | * | 7/1998 | Mazzocco | 623/6 |
| 6,280,471 B1 | * | 8/2001 | Peyman et al. | 623/6.17 |
| 6,299,641 B1 | * | 10/2001 | Woods | 623/6.37 |
| 6,322,589 B1 | * | 11/2001 | Cumming | 623/6.44 |
| 6,324,429 B1 | * | 11/2001 | Shire et al. | 607/54 |

FOREIGN PATENT DOCUMENTS

WO  WO 98/05273  * 2/1998

\* cited by examiner

*Primary Examiner*—Cheryl Miller
(74) *Attorney, Agent, or Firm*—Mathews, Collins, Shepherd and McKay, P.A.

(57) ABSTRACT

A flexible biconvex lens for intra-capsular implantation in an intra-ocular lens capsule of a patient enables the lens refractive properties to be to altered by the transfer of forces from ciliary muscles of the patient to said the flexible biconvex lens. The flexible lens comprises a plurality of holes spaced at equal radial intervals around the periphery of the lens. The plurality of holes promote tissue ingrowths to secure the flexible biconvex lens to the intra-ocular lens capsule without requiring peripheral mechanical extensions, adhesives or mechanical fasteners to said flexible biconvex lens.

10 Claims, 1 Drawing Sheet

FLEXIBLE INTRA-OCULAR LENS OF VARIABLE FOCUS

FIELD OF THE INVENTION

The present invention relates to a flexible intra-ocular lens of variable focus comprising a lens having holes located around the periphery of the lens to allow for the anchoring of the lens in the eye of an animal, in particular, a human.

BACKGROUND OF THE INVENTION

U.S. Pat. No. 6,083,261 issued to Callahan et al. describes an intra-ocular-lens with crossed haptics for securing the lens in the eye. This lens comprises a very thin, deformable optic having two pairs of haptics attached to the optic by means of two stems 180 degrees apart on the circumference of the optic, each tapering to a tip having one haptic each connected to opposite edges of the stem. Each haptic has a footplate defined at the free end of the haptic. Each haptic sweeps about the periphery of the optic so that the angle subtended by a radical line extending from the center of the optic through the center of a footplate and a second radial line extending from the center of the optic through the center of the stem to which it attaches is about 135 degrees. The lens is symmetrical about an axis extending through the opposing stems, with each haptic crossing either over or under the haptic connected to the opposing stem on the same side of the axis. The lens is inserted into the eye by using a previously prepared seriated suture joined by a viscoelastic material to fold the lens in a tubular shape and compress the haptics, inserting the lens in the eye, centering the lens, dissolving viscoelastic material with saline solution, and removing the seriated suture by pulling a free end of the suture left outside the eye during insertion. When released, the footplates of the four haptics lie on a circle concentric with the optic, subtending four substantially equal arcs.

U.S. Pat. No. 5,213,721 issued to Grendahl describes a member of polymer material with a plurality of holes arranged in a predetermined geometric configuration, which can be utilized as either a contact lens, an intra-corneal inlay, an intra-ocular lens, a medical filter, or a like structure with small holes. The holes range in size from 1 angstrom to 12 mm for the passage of nutrients and fluids through the lens, particularly intra-corneal lenses or contact lenses. The '721 patent also describes processes for drawing a boule for producing the holes in optics and filters and a continuous process of drawing a boule for the production of composite materials for optics and filters. The '721 patent does not disclose an intra-ocular lens having a plurality of holes around the periphery.

There exists a need in the art for an alternative method of securing intra-ocular lenses in the eyes of animals, in particular humans and mammals, in addition to the use of crossed haptics.

SUMMARY OF THE INVENTION

The present invention provides for a flexible intra-ocular lens of variable focus comprising an intra-ocular lens comprising a plurality of holes located around the periphery of the lens at the equator.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION

During the course of the description like members will be used to identify like elements according to the different figures which illustrate the invention.

Figure 1:
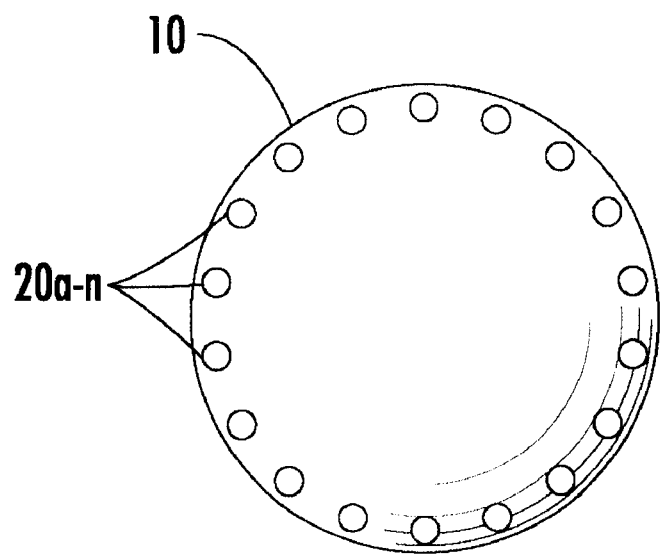
FIG. 1 illustrates a top view of the flexible intra-ocular lens with a plurality of holes around the outer edge of the lens.
Figure 2:
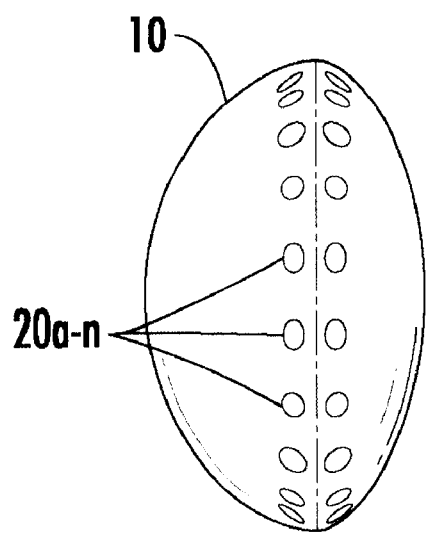
FIG. 2 illustrates a side view of the flexible intra-ocular lens and holes.

Referring now to the drawings the exemplary embodiment of the invention as disclosed in FIGS. 1–2 illustrate the flexible intra-ocular lens 10 in accordance with the teachings of the present invention.

FIG. 1 illustrates a top view of the flexible intra-ocular lens 10 (also referred to herein as "lens") comprising a plurality of holes 20a–20n located around the periphery of the lens.

FIG. 2 illustrates a side view of the flexible intra-ocular lens 10 comprising a plurality of holes 20a–20n located around the periphery of the lens near the outer edge of the lens at the equator. The "equator" of an intra-ocular lens is understood by those in the art as the marginal circumference of the lens.

The lens 10 can be made of a variety of flexible biologically inert and non-toxic materials known to those of ordinary skill in the art of intra-ocular lens. For example, but not by way of limitation, the lens 10 can be made using polymer materials such as hydrophilic plastic (HMMA) or genetic bio-inorganic (bioengineered) intra-ocular lens formed from natural lens stem cells.

Such bioengineered lens tissue can be made by those skilled in the art of tissue engineering using lens stem cells and growing a replacement lens using a compatible scaffold in which to grow the replacement lens such as using human amniotic membranes or other compatible surface. Growth of bioengineered tissued has been performed, for example, by growing corneal epithelium cells. See Ivan R. Schwab and R. Rivkah Isseroff (Jul. 13, 2000) "Bioengineered Corneas—The Promise and the Challenge", The New England Journal of Medicine 343(2) 136–38 and Tsai RJ-F, et al. (Jul. 13, 2000) "Reconstruction of damaged corneas by transplantation of autologous limbal epithelial cells," N. Engl. J. Med 343:86–93.

In alternative embodiments, the lens 19 is made of polymer and/or biological materials. In a more preferred embodiment, the lens is made of biological materials, for example, but not limited to, lens tissue from a human or animal or lens tissue developed or grown from a human or animal stem cells.

The lens dimensions, size and contour will also vary according to the physical and refractive needs. The lens dimensions, size and contour will vary so as to occupy the entire area of lens capsule of the eye after the natural lens has been removed.

The holes 20a–20n of the lens will be plurality of holes in the lens. Preferably, the holes are equally space located near the outer edge of the lens around the periphery. The purpose of the holes is to anchor the lens in the lens capsule by means of the natural capsule tissue growing through said holes 20a–20n and securing said lens.

There will be multiple holes in the periphery of the lens which can vary in number, equally spaced and located near the outer edge of the lens at the equator. The purpose of the holes is to anchor the lens in the lens capsule. The holes in the lens take advantage of the natural structure of the lens capsule to hold the intra-ocular lens. The holes of the intra-ocular lens are placed there to stabilize and anchor the lens in the lens capsule by the formation of tissue occupying drilled area binding the lens to the lens capsule. Residual lens epithelial cells left remaining in the capsule are capable of growing through the -holes of the intra-ocular lenses to secure them in the capsule. For a discussion of the growth of tissue in the- capsule and around lenses see Apple, David J., et al., 1992, "Posterior Capsule Opacification," Survey of Ophthalmology 37(2):73–105. It is also an important feature of the present invention that the intra-ocular lens fill the entire area of the lens capsule to avoid posterior capsule opacification.

The action of the ciliary muscle on the zonules connected to the lens capsule together initiate a change in lens contour of the intra-ocular lens which will vary the focus of the lens.

The lens of the present invention can be made using any available intra-ocular lens by introducing holes along the periphery or equator of the lens or by manufacturing intra-ocular lenses having holes. More particularly, intra-ocular lenses of the present invention have a diameter from about 8 to about 14 mm; a thickness from about 3 to about 6 mm; biconvex posterior radius from about 4 to about 8 mm; a biconvex anterior radius from about 8 to about 11 mm and a refractive index of about 1.4. The curvature, size and thickness of the intra-ocular lenses may vary with the physical and refractive requirements of the patient. It should be appreciated that the intra-ocular lens of the present invention may have a variety of sizes and shapes which depend upon the lens power required, the material used and the physical and anatomical limitations of the particular eye and the lens capsule.

The intra-ocular lenses of the present invention is molded using conventional methods known in the art and the holes are generated by drilling, laser or by being molded with processes incorporated in the mold to generate the holes. The holes will be placed about 2 mm inside the edge of the periphery or equator of the lens. The holes will vary in size from about 1.5 to about 3 mm in diameter. The holes are preferably equally spaced from about 2 to about 3 mm apart.

The lens is surgically inserted into an animal's eye using standard intra-ocular lens replacement techniques. For example, but not by way of limitation, methods of intra-ocular lens replacement are set forth in U.S. Pat. No. 4,888,015, incorporated herein by reference. Briefly, the procedure includes the use of a horizontal capsulotomy incision to allow for the removal of the lens from the lens capsule without destruction or removal of any portion of the capsule. No sutures or other unnatural materials are required. A replacement lens is then inserted into the empty lens capsule occupying the total area inside the lens capsule.

Various modifications can be made to the present application without departing from the apparent scope hereof The present embodiments are, therefore, to be considered as illustrative and not restrictive, the scope of the invention being indicated by the claims rather than from the foregoing description, and all changes which come within the meaning and range of equivalence of the claims and therefore intended to be based therein.

Various references are cited above and are incorporated by reference in their entirety.

What is claimed is:

1. A flexible lens for intra-capsular implantation in an intra-ocular lens capsule of a patient, the flexible lens comprising:

a flexible biconvex lens defined by a biconvex posterior radius of curvature between about 4 millimeters to about 8 millimeters and a biconvex anterior radius of curvature between about 8 millimeters to about 11 millimeters; and, a plurality of holes within said flexible biconvex lens, spaced at approximately equal radial intervals around periphery of said flexible biconvex lens;

wherein and said plurality of holes promote tissue ingrowths to secure said flexible biconvex lens to the intra-ocular lens capsule without requiring peripheral mechanical extensions, adhesives or mechanical fasteners to said flexible biconvex lens and enable transfer of forces from ciliary muscles of the patient to said flexible biconvex lens and thereby alter refractive properties of said flexible biconvex lens.

2. The flexible lens as recited in claim 1 wherein the plurality of holes are located approximately 2 millimeters from the outer edge of the lens at an equator of said lens.

3. The flexible lens as recited in claim 1 wherein the plurality of holes are between about 1.5 millimeters to about 3 millimeters in diameter.

4. The flexible lens as recited in claim 1 wherein the plurality of holes number between approximately 12 to 16 holes.

5. The flexible lens as recited in claim 1 wherein the plurality of holes are essentially spaced evenly apart at about 2 mm to about 3 mm.

6. The flexible lens as recited in claim 1 wherein the flexible biconvex lens has a refractive index of approximately 1.4.

7. The flexible lens as recited in claim 1 wherein the flexible biconvex lens is a polymer.

8. The flexible lens as recited in claim 7 wherein the polymer is a hydrophilic plastic.

9. The flexible lens as recited in claim 1 wherein the flexible biconvex lens is a bioengineered material.

10. The flexible lens as recited in claim 1 wherein the flexible biconvex lens is a genetic bio-inorganic material.

* * * * *